United States Patent [19]

Warriner

[11] Patent Number: Plant 5,901

[45] Date of Patent: Mar. 17, 1987

[54] ROSE PLANT JACPOP

[75] Inventor: William A. Warriner, Tustin, Calif.

[73] Assignee: Jackson & Perkins Company, Medford, Oreg.

[21] Appl. No.: 771,849

[22] Filed: Sep. 3, 1985

[51] Int. Cl.[4] ..... A01H 5/00

[52] U.S. Cl. ..... Plt./11

[58] Field of Search ..... Plt./11, 15

*Primary Examiner*—Robert E. Bagwill

*Attorney, Agent, or Firm*—Manford R. Haxton

[57] ABSTRACT

A hybrid tea rose variety having a vigorous upright habit of growth, suitability for garden cut flowers, unusual flower colors that change with flower maturity, glossy green foliage and a light pleasing flower fragrance.

1 Drawing Figure

This present invention relates to a new and distinct variety of rose plant of the hybrid tea class which was originated by crossing the variety Bridal Pink, U.S. Plant Pat. No. 2,851, with an unnamed variety.

The primary objective of this breeding was to produce a new rose variety in the hybrid tea class with good vigor and in the yellow flower group. This objective was substantially achieved along with other desirable improvements as evidenced by the following unique combination of characteristics which are outstanding in the new variety and which distinguish it from its parents as well as from all other varieties of which I am aware:

1. A vigorous upright habit of growth;
2. Production of large showy flowers;
3. Strong flower stem suitable for garden cut flowers;
4. A distinctive and attractive color of the flowers beginning in the bud with a bright yellow overcast with pink bands, opening to a bright solid yellow fading to a creamy white fringed with pink at flower maturity;
5. Light fragrance; and
6. Dark green glossy foliage.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated:

Parentage:

*Seed parent.*—Bridal Pink, U.S. Plant Pat. No. 2,851.

*Pollen parent.*—Unnamed variety.

Classification:

*Botanical.*—Rosa hybrid.

*Commercial.*—Hybrid tea.

FLOWER

Observations made from specimens grown in a greenhouse at Irvine, Calif. in June.

Blooming habit: Continuous.

Bud:

*Size.*—1½" when petals start to unfurl.

*Form.*—Pointed ovoid.

*Color.*—When sepals first divide, Yellow (Yellow 12B to 13C) with the outer petals overlain with bands of Pink (41 B to C); when half blown, upper side of petals Yellow (12C to 13C) with a tint of Pink on the outer petals (49C to 49D); lower side of petals essentially the same color (Yellow 12C to 13C), except for the outer petals which have little or no Pink.

*Sepals.*—Color: Green (138B). Three appendaged sepals lightly appendaged. Two unappendaged sepals hairy edge.

*Receptacle.*—Color: Green 138B. Shape: Funnel. Size: Large. Surface: Slightly hairy.

*Peduncle.*—Length: Short. Surface: Glandular. Color: Medium Green, bronzy. Strength: Stiff, erect.

Open bloom:

*Size.*—Large. Average open size 4".

*Borne.*—Singly, or several together.

*Stems.*—Long, strong.

*Form.*—When first open, high center. Permanence: flattens, outer petals curl back.

*Petalage.*—Number of petals under normal conditions: 30.

*Color.*—Center of flower: Upper side of petals, Yellow 12B to 13C fading as the flower matures to allow expression of a pale pink 49C to 49D; reverse side of petals, Yellow 12C to 13C fading as the flower matures to a very pale pink 36D. Base of petals, Yellow 12A to 13B. Major color: Yellow 12A to 13B which fades to allow the expression of pale pink 49C to 49D.

*Discoloration.*—General tonality at end of first day: No change. Third day: Lightens to 12C to 13C.

*Fragrance.*—Slight.

Petals:

*Texture.*—Thick.

*Shape.*—Wide, oval.

*Form.*—Tips slightly recurved with outer petal edges slightly quilled.

*Arrangement.*—Imbricated. Petaloids in center, few.

*Persistence.*—Drop off cleanly.

*Lastingness.*—On the plant, long. As cut flower, long.

Reproductive parts:

*Anthers.*—Medium. Color: Yellow. Arrangement: Regular around styles.

*Filaments.*—Color: Yellow.

*Pollen.*—Gold yellow.

*Styles.*—Color: Pink.

*Stigmas.*—Color: Yellow.

PLANT

Form: Bush.

Growth: Vigorous.

Foliage: Number of leaflets on normal mid-stem leaves: 5.

*Size.*—Large.

*Quantity.*—Normal.

*Color.*—New foliage: Green overlain with Greyed Purple (184A). Old foliage: Green 137A.

Leaflets:

*Shape.*—Oval pointed.

*Texture.*—Leathery, glossy.

*Edge.*—Serrated.

*Serration.*—Single, small.

*Petiole.*—Rachis: Color: Reddish. Upperside: Upper ridge having stipitate glands. Underside: Rough, with prickles.

*Stipules.*—Medium, bearded.

*Disease resistance.*—Susceptible to mildew, under normal growing conditions at Irvine, Calif.

Wood:

*New wood.*—Color: Reddish. Bark: Smooth, but covered with stipitate glands and hair.

*Old wood.*—Color: Green. Bark: Smooth.

Prickles:

*Quantity.*—On main canes from base: Ordinary. On laterals from main canes: Ordinary.

*Form.*—Slightly hooked downward.

*Color when young.*—Red.

Small prickles:

*Quantity.*—On main stalks, none. On laterals, few.

*Color.*—Brown.

I claim:

1. A new and distinct variety of rose plant of the hybrid tea class, substantially as herein shown and described, characterized particularly as to novelty by the unique combination of a vigorous upright habit of growth, suitability for garden cut flowers, unusual flower colors that change with flower maturity, glossy green foliage and a light pleasing flower fragrance.

* * * * *

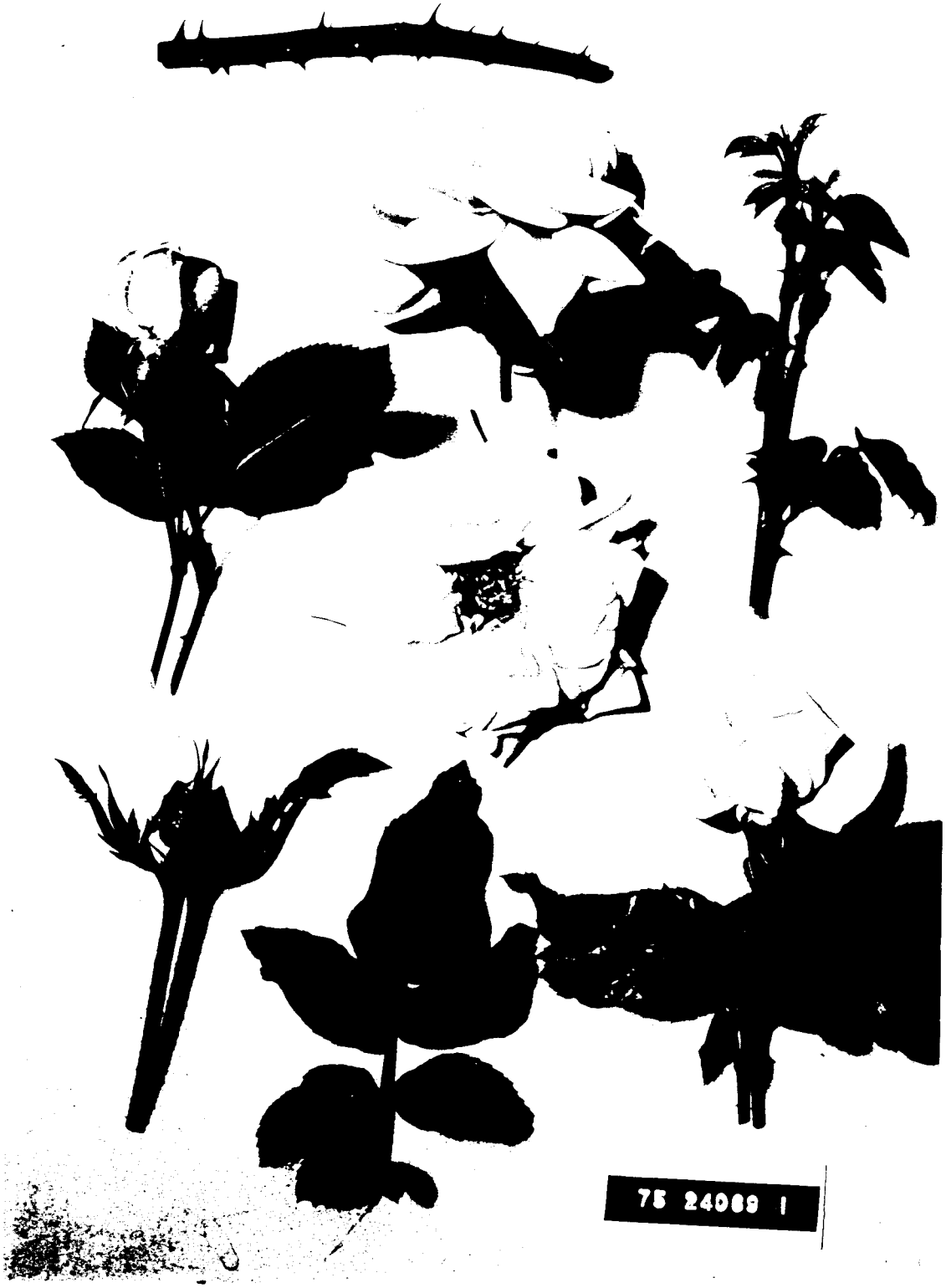
75 24089 1